United States Patent [19]

Cooper et al.

[11] Patent Number: 4,505,919
[45] Date of Patent: Mar. 19, 1985

[54] ANTIFUNGAL S-ARYLMETHYL- AND S-HETEROCYCLYLMETHYL ETHERS OF 2-ARYL-3-MERCAPTO-1-(1H-1,2,4-TRIAZOL-1-YL) PROPAN-2-OLS

[75] Inventors: Kevin Cooper, Ramsgate; Kenneth Richardson; Peter J. Whittle, both of Canterbury, all of England

[73] Assignee: Pfizer Inc., New York, N.Y.

[21] Appl. No.: 479,526

[22] Filed: Mar. 28, 1983

[30] Foreign Application Priority Data

Oct. 9, 1982 [GB] United Kingdom ............... 8228920

[51] Int. Cl.$^3$ .................... C07D 401/10; A61K 31/44
[52] U.S. Cl. .................................... 514/340; 546/276; 548/262; 548/252; 548/193; 514/370; 514/381; 514/383
[58] Field of Search ....................... 548/262, 252, 193; 546/276; 424/263, 270, 273 R, 269

[56] References Cited

U.S. PATENT DOCUMENTS 4,036,970  7/1977  Walker et al. ...................... 548/341

FOREIGN PATENT DOCUMENTS 46633  8/1980  European Pat. Off. ............ 548/262
40345  11/1981  European Pat. Off. .
54974  6/1982  European Pat. Off. .
61835  10/1982  European Pat. Off. .
2908378  9/1980  Fed. Rep. of Germany .

Primary Examiner—Jane T. Fan
Attorney, Agent, or Firm—Charles J. Knuth; Albert E. Frost; Peter C. Richardson

[57] ABSTRACT

Compounds of the formula:

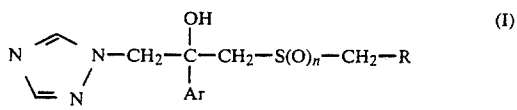

wherein
Ar is phenyl substituted by from 1 to 3 substituents, each substituent being independently halo or $CF_3$;
n is 0 or 1; and
R is a phenyl or a phenyl group substituted by from 1 to 3 substituents, each substituent being independently halo, $CF_3$, $C_1$–$C_4$ alkoxy, $C_2$–$C_5$ alkoxy-carbonyl or $C_1$–$C_4$ alkylthio, or a 5 or 6 membered aromatic heterocyclic group which may optionally be substituted;

and their pharmaceutically acceptable salts are antifungal agents useful in combatting fungal infections in humans.

8 Claims, No Drawings («4,505,919»)

ANTIFUNGAL S-ARYLMETHYL- AND S-HETEROCYCLYLMETHYL ETHERS OF 2-ARYL-3-MERCAPTO-1-(1H-1,2,4-TRIAZOL-1-YL) PROPAN-2-OLS

BACKGROUND OF THE INVENTION

This invention relates to novel triazole derivatives which have antifungal activity and are useful in the treatment of fungal infections in humans.

In particular the invention relates to certain 3-heterocyclylmethylthio- and 3-arylmethylthio-1-triazolyl-2-propanol derivatives which are particularly effective as oral and topical agents for the treatment of fungal diseases in humans and other animals, and to pharmaceutical compositions containing such compounds.

Concurrently filed U.S. patent applications of Richardson and Gymer entitled "Antifungal S-Ethers of 2-Aryl-3-Mercapto-1-(1H-1,2,4-Triazol-1-yl)Propan-2-Ols and Corresponding Sulfoxides and Sulfones", and of Richardson and Whittle entitled "Triazole Antifungal Agents", and identified by Ser. Nos. 479,524, filed 3/28/83 and 479,525, filed 3/28/85, respectively, are directed to related S-ethers of 2-aryl-3-mercapto-1-(1H-1,2,4-triazol-1-yl)-propan-2-ols.

European patent application No. 0061835 discloses a broad class of triazole and imidazole compounds having the general formula:

$$\text{Az}-\underset{\underset{R^7}{|}}{\overset{\overset{R^6}{|}}{C}}-\underset{\underset{R^1}{|}}{\overset{\overset{OR^3}{|}}{C}}-\underset{\underset{R^5}{|}}{\overset{\overset{R^4}{|}}{C}}-X-R^2 \quad (A)$$

wherein $R^1$ and $R^2$, which may be the same or different, are hydrogen, alkyl, optionally substituted cycloalkyl, cycloalkylmethyl, alkenyl, heterocyclyl, aryl or aralkyl optionally substituted with halogen, nitro, alkyl, haloalkyl, alkoxy, phenyl, phenoxy, benzyl, benzyloxy, halophenyl or haloalkoxy; $R^3$ is hydrogen, alkyl, alkenyl, alkynyl, aralkyl or acyl; $R^4$ and $R^5$, which may be the same or different are hydrogen, alkyl, alkenyl or optionally substituted aryl; $R^6$ and $R^7$, which may be the same or different are hydrogen, alkyl, alkenyl or optionally substituted aryl; X is oxygen or sulfur or is SO or $SO_2$ and Az is a 1,2,4- or 1,3,4-triazole or imidazole ring; and isomers, acid addition salts and metal complexes thereof.

The compounds are stated to possess fungicidal activity, principally as plant fungicides, and also to be plant growth regulators. There is also a brief reference that the compounds are useful for the treatment of candidiasis and human dematophyte infections.

We have discovered that a particular class of non-exemplified compounds within formula (A) wherein $R^3$, $R^4$, $R^5$, $R^6$ and $R^7$ are H, X is S or SO and $R^2$ is arylmethyl are surprisingly particularly effective as human antifungal agents and this property is not shared by the compounds wherein $R^2$ is aryl, which are the only compounds where X is S exemplified in the European patent.

The invention also includes the corresponding heterocyclylmethyl derivatives which are not within the scope of the European patent application No. 0061835.

SUMMARY OF THE INVENTION

According to the invention, there are provided compounds of the formula:

$$\underset{N}{\overset{N}{\underset{\|}{\diagdown}}}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!}}$$

$$N \diagup\!\!\diagdown N-CH_2-\underset{\underset{Ar}{|}}{\overset{\overset{OH}{|}}{C}}-CH_2-S(O)_n-CH_2-R \quad (I)$$

wherein

Ar is phenyl substituted by from 1 to 3 substituents, each substituent being independently halo or $CF_3$;
n is 0 or 1; and
R is a phenyl or a phenyl group substituted by from 1 to 3 substituents, each substituent being independently halo, $CF_3$, $C_1$–$C_4$ alkoxy, $C_2$–$C_5$ alkoxycarbonyl or $C_1$–$C_4$ alkylthio, or a 5 or 6 membered aromatic heterocyclic group which may optionally be substituted;

and salt forms thereof.

"Halo" means F, C, Br or I.

Heterocyclic groups include 5 and 6 membered aromatic heterocyclic groups linked to the $-CH_2-$ group via a ring carbon atom. Particular examples include 2-imidazolyl, 4-thiazolyl, 3-thienyl, 2-furyl, 3-(1,2,4-triazolyl), 5-tetrazolyl, 2-(1,3,4-thiadiazolyl), 2-, 3- and 4-pyridyl and 2- and 4-pyrimidinyl. Substituents for the heterocyclic ring include one or more halo, $CF_3$, $C_1$–$C_4$ alkyl, $C_1$–$C_4$ alkoxy, amino, mono or di($C_1$–$C_4$ alkyl) amino, $C_2$–$C_5$ alkanoylamino, hydroxy or thio groups.

Alkyl, alkoxy and alkanoyl groups may be straight or branched chain where appropriate.

The invention also provides a pharmaceutical composition comprising a compound of the formula (I) or a pharmaceutically acceptable salt thereof, together with a pharmaceutically acceptable diluent or carrier.

The invention further provides a method for treating fungal infections in animals, including humans which comprises administering a compound of the formula (I) or a pharmaceutically acceptable salt thereof.

A preferred substituted phenyl group for Ar is halo- or dihalophenyl, especially 2,4-dichlorophenyl.

n is preferable 0.

R is preferably a heterocyclic group, especially a 2-pyridyl, 1-methyl-2-imidazolyl, 2-amino-4-thiazolyl or 1-methyl-5-tetrazolyl group.

Particularly preferred individual compounds of the invention include:

1-[2-(2,4-Dichlorophenyl)-2-hydroxy-3-(2-pyridylmethylthio)propyl]1,2,4-triazole,
1-[2-(2,4-Dichlorophenyl)-2-hydroxy-3-(1-methyl-2-imidazolylmethylthio)propyl]1,2,4-triazole,
1-[2-(2,4-Dichlorophenyl)-2-hydroxy-3-(2-amino-4-thiazolylmethylthio)propyl]1,2,4-triazole, and
1-[2-(2,4-Dichlorophenyl)-2-hydroxy-3-(1-methyl-5-tetrazolylmethylthio)propyl]1,2,4-triazole.

DETAILED DESCRIPTION OF THE INVENTION

The compound of formula (I) can be obtained by a number of different processes according to the invention.

1. In one process, the compounds of the formula (I) in which n is 0 can be prepared from an oxirane of the formula:

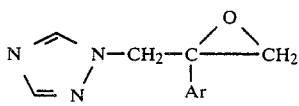

(II)

by reaction with a thiol of the formula:

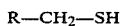 (III)

wherein Ar and R are as previously defined.

The reaction can be achieved under a variety of different conditions, depending to some extent on the precise nature of the reactants. Generally it is possible to achieve the reaction in a convenient manner by simply heating the oxirane (II), as its free base, with excess of the thiol (III) in an organic solvent, e.g. dioxan. A period of up to three days at reflux temperature is generally sufficient; however, addition of a catalytic amount of dilute sodium hydroxide solution often gives improved yields and reduces reaction times. The product can be isolated and purified by conventional procedures, for example, by evaporating the solvent, taking the product up in a water-immiscible organic solvent, extracting the solution with dilute sodium hydroxide or potassium carbonate solution to remove unreacted thiol, drying and evaporating the solvent. The product may be further purified, if desired, by crystallization or by chromatography.

As an alternative procedure, the oxirane as its methanesulphonate salt and the thiol are heated together in an organic solvent, e.g. N,N-dimethylformamide or tetrahydrofuran, in the presence of a base, e.g. potassium carbonate or sodium hydride. A temperature of from 60° to 80° C. is generally employed, and under these conditions the reaction is generally substantially complete within a few hours. The product is isolated and purified as previously described.

As a further variation the oxirane as its methanesulphonate salt is heated with excess of the heterocyclic thiol under reflux in glacial acetic acid for a period of several hours.

The oxiranes (II) can be obtained by conventional methods, typically from the corresponding ketones (IV):

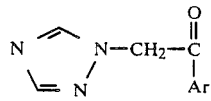 (IV)

by reaction with dimethyloxosulphonium methylide prepared from trimethylsulphoxonium iodide and either sodium hydride in dimethylsulphoxide or using cetrimide and sodium hydroxide in a mixture of water and toluene.

The reaction using sodium hydride is typically achieved by adding dry powdered trimethylsulphoxonium iodide to a suspension of sodium hydride in dimethylsulphoxide. After stirring for 30 minutes at room temperature, the ketone (IV) is added in an approximately equimolar amount in dimethylsulphoxide. The reaction mixture may be warmed to accelerate the reaction and after several hours at 50°-80° C., the product can be isolated by conventional procedures.

The reaction utilizing cetrimide is typically achieved by stirring the ketone (IV), trimethylsulphoxonium iodide and cetrimide vigorously together in a mixture of toluene and sodium hydroxide solution for about an hour at up to about 100° C. The oxirane product can then be isolated by conventional procedures.

When Ar is a phenyl group containing no ortho substituent, the cetrimide route should be used.

The ketones (IV) are either known compounds or can be prepared by procedures analogous to those of the prior art. The preparation of 2-(1H-1,2,4-triazol-1-yl)-2'-4'-dichloroacetophenone from 2-bromo-2',4'-dichloroacetophenone, 1,2,4-triazole and potassium carbonate is, for example, described in Example 1 of British Patent Specification No. 1512918, which utilizes acetonitrile as the solvent under reflux for 20 hours. We have found that this type of reaction is generally best carried out in acetone at 0°-20° C., when it is generally complete in a shorter period of time, e.g. 4 hours or less.

The thiols of formula III are generally known compounds or they are prepared from readily available starting materials by conventional reactions.

2. In an alternative synthesis the compounds of the formula (I) where n is 0 are prepared from a thiol of formula:

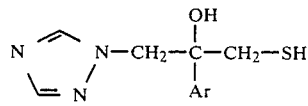 (V)

by reacting with a halide of the formula:

 (VI)

wherein Ar and R are as previously defined and X is chloro, bromo or iodo. The reaction is generally carried out by stirring the reactants together in an inert organic solvent, e.g. N,N-dimethylformamide, in the presence of a base e.g. NaOH or K$_2$CO$_3$. A period of a few hours at room temperature is generally sufficient, but if necessary the reaction mixture can be heated to accelerate the reaction. The product can be isolated and purified by conventional procedures.

The thiols of formula (V) are prepared from the oxiranes of formula (II) by first reacting with thiolacetic acid and then deacylating the resulting product e.g. using sodium ethoxide in ethanol followed by acidification with hydrochloric acid.

The halides of formula (VI) are generally known compounds or they are prepared by conventional procedures in accordance with literature precedents.

3. The compounds of the formula (I) in which n is 1 (sulphoxides) can be prepared by the controlled oxidation, of the corresponding compounds in which n is 0.

The preferred oxidizing agent is m-chloroperbenzoic acid: approximately one equivalent should be used to prepare the sulphoxides.

In a typical procedure the thio compound is dissolved in a mixture of isopropanol and chloroform (1:1, v/v) and the solution is cooled to below 5° C. in an ice bath. Slightly less than 1 equivalent of m-chloroperbenzoic acid is added in portions over a few minutes. The mixture is then stirred for about two hours. If thin layer chromatography indicates unreacted starting material, a further small quantity of m-chloroperbenzoic acid (up to a total of 1 equivalent) is added. The sulphoxides have two asymmetric centres and thus exist in two diastereoisomeric forms. Thus the sulphoxide product of the oxidation, which can be isolated by conventional procedures, will be a mixture of the two diastereoisomers. If desired, the diastereoisomers can be separated by column chromatography, e.g. on silica, since they usually differ in polarity.

4. In the case where the heterocyclic ring contains substituted groups, conventional chemical transformation reactions can be used to prepare simple derivatives and related compounds. Thus for example, when the heterocyclic ring contains an amino group, a conventional acetylation reaction (e.g. using acetic anhydride in pyridine) can be employed to prepare the N-acetyl derivative. Other transformation reactions and the reagents and conditions required for their performance will be well known to those skilled in the art.

All the compounds of the invention contain at least one chiral centre, and the invention includes both resolved and unresolved forms.

For pharmaceutical use, acceptable acid addition salts of the compounds of the formula (I) include those formed from strong acids which form non-toxic acid addition salts, such as hydrochloric, hydrobromic, sulphuric, nitric, oxalic and methanesulphonic acids.

The salts are obtained by conventional procedures, e.g. by mixing solutions containing equimolar amounts of the free base and desired acid, and the required salt is collected by filtration, if insoluble, or by evaporation of the solvent.

The compounds of the formula (I) and their pharmaceutically acceptable salts are antifungal agents, useful in combatting fungal infections in animals, including humans. For example, they are useful in treating topical fungal infections in man caused by among other organisms, species of Candida, Trichophyton, Microsporum, or Epidermophyton, or in mucosal infections caused by *Candida albicans* (e.g. thrush and vaginal candidiasis). They can also be used in the treatment of systemic fungal infections caused by, for example, *Candida albicans, Cryptococcus neoformans, Aspergillus fumigatus,* Coccidioides, Paracoccidiordes, Histoplasma or Blastomyces.

The in vitro evaluation of the antifungal activity of the compounds can be performed by determining the minimum inhibitory concentration (m.i.c.) of the test compounds in a suitable medium at which growth of the particular micro-organism fails to occur. In practice, a series of agar plates, each having the test compound incorporated at a particular concentration are inoculated with a standard culture of, for example, *Candida albicans* and each plate is then incubated for 48 hours at 37° C. The plates are then examined for the presence of growth of the fungus and the appropriate m.i.c. value is noted. Other micro-organisms used in such tests can include *Cryptococcus neoformans, Aspergillus fumigatus,* Trichophyton spp; Microsporum spp; *Epidermophyton floccosum, Coccidioides immitis,* and *Torulopsis glabrata.*

The in vivo evaluation of the compounds can be carried out at a series of dose levels by intraperitoneal or intravenous injection or by oral administration, to mice which are inoculated with a strain of *Candida albicans*. Activity is based on the survival of a treated group of mice after the death of an untreated group of mice following 48 hours observation. The dose level at which the compound provides 50% protection against the lethal effect of the infection is noted.

For human use, the antifungal compounds of the formula (I) can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the antifungal compounds of the formula (I) is from 0.1 to 10 mg/kg (in divided doses) when administered by either the oral or parenteral route. Thus tablets or capsules of the compounds contain from 5 mg to 0.5 g of active compound for administration singly or two or more at a time as appropriate. In any event the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

Alternatively, the antifungal compounds of formula (I) can be administered in the form of a suppository or pessary, or they can be applied topically in the form of a lotion, solution, cream, ointment or dusting powder. For example, they can be incorporated into a cream consisting of an aqueous emulsion of polyethylene glycols or liquid paraffin; or, at a concentration between 1 and 10%, into an ointment consisting of a white wax or white soft paraffin base together with such stabilizers and preservatives as may be required.

The compounds of the invention also have activity against a variety of plant pathogenic fungi, including, for example, various rusts, mildews and moulds, and the compounds are thus useful for treating plants and seeds to eradicate or prevent such diseases.

The following Examples illustrate the invention:

EXAMPLE 1

1-[3-(4-Chlorobenzylthio)-2-(2,4-dichlorophenyl)-2-hydroxypropyl]-1,2,4-triazole 2-(2,4-Dichlorophenyl)-2-(1H-1,2,4-triazol-1-ylmethyl)oxirane methanesulphonate salt (0.336 g, 1 mmole), 4-chlorobenzyl mercaptan, (0.159 g, 1 mmole) and anhydrous potassium carbonate (0.414 g, 3 mmole) were stirred in dry N,N-dimethylformamide (15 ml) at 70° C. for 72 hours. The reaction mixture was diluted with water (70 ml) and extracted with ethyl acetate (2×70 ml). The extracts were combined and evaporated to give an oil which crystallized on standing. Recrystallization from a mixture of ethyl acetate and n-hexane gave the title compound (0.23 g, 53%) m.p. 106°–107° C.

Analysis %:
Found: C, 50.74; H, 3.56; N, 10.14.
$C_{18}H_{16}Cl_3N_3OS$ requires: C, 50.42; H, 3.76; N, 9.80.

EXAMPLE 2

1-[2-(2,4-Dichlorophenyl)-2-hydroxy-3-(2-pyridylmethylthio)propyl]-1,2,4-triazole 1-[2-(2,4-Dichlorophenyl-2-hydroxy-3-mercaptopropyl-1,2,4-triazole (0.5 g, 1.64 mmole) and anhydrous potassium carbonate (0.69 g, 5 mmole) were stirred together in N,N-dimethylformamide (10 ml) and the mixture was cooled in ice. 2-Chloromethylpyridine hydrochloride (0.3 g, 1.83 mmole) was added and stirring in ice was continued for a further 1 hour. The reaction mixture was then poured into a mixture of dichloromethane (50 ml) and water (50 ml) and the organic layer was separated. The aqueous layer was extracted a further 5 times with dichloromethane (50 mls in total) and the combined organic extracts were dried over magnesium sulphate and evaporated. The residue was chromatographed on silica, eluting with a mixture of dichloromethane and methanol (97:3), to give the title compound as a colourless gum (0.58 g, 90%). Treatment of the product with ethereal hydrogen chloride gave the dihydrochloride monohydrate as a hygroscopic white solid, m.p. 136°–141° C.

Analysis %:
Found: C, 41.97; H, 3.92; N, 11.68.
$C_{17}H_{20}Cl_4N_4O_2S$ requires: C, 41.98; H, 4.11; N, 11.5.

EXAMPLES 3–10

The following compounds were prepared by the general procedures described in Examples 1 and 2 using the appropriate starting materials.

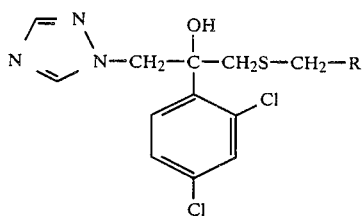

| Example No. | R | m.p. °C. | C | H | N |
|---|---|---|---|---|---|
| 3 | (furyl, 2-methyl) | 56–60 | 46.00 (45.58 | 3.69 3.61 | 8.52 8.86) |
| 4 | (N-methylpyrazolyl) | 115–17 | 48.2 (48.28 | 4.27 4.39 | 17.59 17.99) |
| 5 | (2-amino-thiazolyl) | 151–6 | 43.25 (43.27 | 3.62 3.61 | 17.23 16.83) |
| 6 | (phenyl) | 52–4[c] | 49.56 (49.60 | 4.16 3.95 | 8.36 8.68) |
| 7 | (3-chlorophenyl) | 134–6[b] | 46.10 (46.47 | 3.70 3.68 | 9.26 9.03) |
| 8 | (4-methoxyphenyl) | 124–6[b] | 49.12 (49.52 | 4.44 4.37 | 8.96 9.12) |
| 9 | (4-carbomethoxyphenyl) | 102–5[c] | 49.46 (48.72 | 4.15 3.90 | 7.54 7.75) |
| 10 | (N-methyltetrazolyl) | 155–156.5 | 42.16 (42.0 | 3.86 3.75 | 24.63 24.5) |

[a] dihydrochloride, monohydrate
[b] monohydrochloride
[c] monooxalate

EXAMPLE 11

1-[3-(4-Chlorobenzylsulphinyl)-2-(2,4-dichlorophenyl)-2-hydroxypropyl]-1,2,4-triazole 1-[3-(4-Chlorobenzylthio-2-(2,4-dichlorophenyl)-2-hydroxypropyl]-1,2,4-triazole (2.15 g, 5 mmole) was dissolved in a mixture of dichloromethane (30 ml) and isopropanol (30 ml). The solution was stirred and cooled in ice. To this solution was added metachloroperbenzoic acid (85% pure; 1.02 g, 5 mmole) in three portions over a period of five minutes. The reaction was allowed to proceed for 24 hours at room temperature. Dichloromethane (100 ml) was added and the organic layer separated and washed twice with a solution of sodium carbonate (2.5 g) and sodium metabisulphite (2.5 g) in water (100 ml). The organic layer was then dried over magnesium sulphate and evaporated to give a mixture of the two sulphoxide diastereomers as an oil which crystallized on standing. Recrystallization from ethyl acetate gave the title compound as a single pure isomer (t.l.c.: Rf 0.30; silica; ethyl acetate, methanol, ammonium hydroxide, 90:10:1) (0.34 g, 15%) m.p. 193°–195° C.

Analysis %:
Found: C, 48.58; H, 3.63; N, 9.44.
$C_{18}H_{16}Cl_3N_3O_2S$ requires: C, 48.61; H, 3.63; N, 9.45.

The residual mixture obtained by evaporation of the mother liquors was chromatographed on silica eluting with a mixture of ethyl acetate, methanol and concentrated ammonium hydroxide (90:10:1). The relevant fractions were combined and evaporated to give the second isomer (t.l.c.: Rf 0.20; silica; ethyl acetate; methanol; ammonium hydroxide, 90:10:1) which was recrystallized from ethyl acetate (0.25 g, 12%) m.p. 191°–193° C.

Analysis %:
Found: C, 48.75; H, 3.70; N, 9.44.
$C_{18}H_{16}Cl_3N_3O_2S$ requires: C, 48.61; H, 3.63; N, 9.45.

EXAMPLE 12

The following illustrate pharmaceutical compositions for the treatment of fungal infections:

(1) Capsule: 71 parts by weight of the compound of Example 1 are granulated with 3 parts maize starch and 22 parts lactose and then a further 3 parts of maize starch and 1 part magnesium stearate are added. The mixture is regranulated and filled into hard gelatin capsules.

(2) Cream: 2 parts by weight of the compound of Example 1 are dissolved in 10 parts of propylene glycol and mixed into 88 parts of a vanishing cream base.

(3) Pessary: 2 parts by weight of the compound of Example 1 are suspended in 98 parts of a warm liquified suppository base which is poured into moulds and allowed to solidify.

PREPARATION 1

Preparation of 2-(2,4-Dichlorophenyl)-2-(1H-1,2,4-triazol-1-ylmethyl)-oxirane

Sodium hydride (3.78 g, 0.079 mole as 50% dispersion in oil) was suspended, with stirring, in 20 ml of dry diethyl ether. The ether was then removed by decantation, and the sodium hydride was dried in a stream of dry nitrogen. 100 Ml of dry dimethyl sulphoxide was added followed by 17.34 g (0.079 mole) of dry powdered trimethylsulphoxonium iodide, in portions, over 15 minutes. The resulting mixture was stirred for 30 minutes at room temperature (20° C.). 2-(1H-1,2,4-Triazol-1-yl)-2',4'-dichloroacetophenone (18.33 g, 0.072 mole) as a solution in 50 ml of dry dimethyl sulphoxide was then added. The mixture was heated at 60° C. for 3 hours and allowed to stand at room temperature overnight. The reaction mixture was cooled and quenched in ice and the product was then extracted into ethyl acetate (600 ml). The ethyl acetate layer was separated, dried over magnesium sulphate, and concentrated to give a red gum. Column chromatography of the gum on silica, eluting with ether, gave 6.62 g (34.4%) of the title compound as a gum.

PREPARATION 2

Preparation of 1-[2-(2,4-dichlorophenyl)-2-hydroxy-3-mercaptopropyl]-1H-1,2,4-triazole 2-(2,4-Dichlorophenyl)-2-(1H-1,2,4-triazol-1-ylmethyl)-oxirane, 5 g, (0.0185 mole) was heated under mild reflux in thiolacetic acid ($CH_3COSH$) (5 ml) for three hours. The mixture was then cooled and added to a mixture of ice-cooled saturated sodium bicarbonate solution (200 ml) and ethyl acetate (200 ml) and the aqueous layer was separated. The organic layer was washed a further four times with ice-cooled saturated sodium bicarbonate solution (200 ml in total), dried over magnesium sulphate and evaporated to give a red gum which was dissolved in ethanol (20 ml). This solution was added dropwise over 15 minutes to a stirred and ice-cooled solution of sodium ethoxide (3.78 g, 0.0556 mole) in ethanol (100 ml). After one hour the mixture was poured into 1N hydrochloric acid (100 ml) and this solution was then neutralized by addition of solid sodium bicarbonate. Extraction with dichloromethane (6×50 ml), drying over magnesium sulphate, and evaporation of the combined extracts gave a gum which was chromatographed on silica, eluting with ethyl acetate, to give after one recrystallization from ethyl acetate/hexane the title compound, yield 2.3 g, m.p., 139°–142.5° C.

Analysis %:
Found: C, 43.3; H, 3.7; N, 14.0.
Calculated for $C_{11}H_{11}Cl_2N_3OS$: C, 43.4; H, 3.6; N, 13.8.

TEST RESULTS (a) The compounds of the Examples were tested in vivo by administration to mice according to the procedures described herein. The dose levels providing 50% protection ($PD_{50}$) were as follows:

| Example No. | $PD_{50}$ (mg/kg) |
| --- | --- |
| 1 | 0.8 (i.v.) |
| 2 | 0.4 (p.o.) |
| 3 | 2.2 (p.o.) |
| 4 | 0.2 (p.o.) |
| 5 | 0.9 (p.o.) |
| 6 | 1.5 (p.o.) |
| 7 | 2.2 (p.o.) |
| 8 | 2.2 (p.o.) |
| 9 | 1.5 (p.o.) |
| 10 | 0.6 (p.o.) |
| 11 | 4.4 (p.o.) |

(b) Comparative test results were obtained for the following compounds:

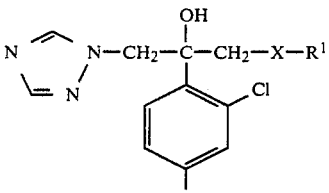

| X | $R^1$ | $PD_{50}$ mg/kg |
| --- | --- | --- |
| —S— | 4-chlorophenyl | >10 (p.o.) |
| —S— | 4-($NHCO_2C_2H_5$)phenyl | >10 (p.o.) |
| —SO— | 4-chlorophenyl | >10 (p.o.) |
| —O— | —$CH_2$-4-chlorophenyl | >5 (p.o.) |

-continued

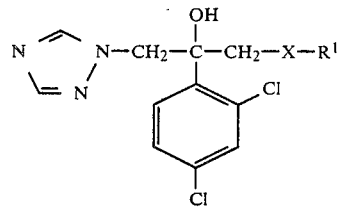

| X | R¹ | PD₅₀ mg/kg |
|---|---|---|
| —O— | 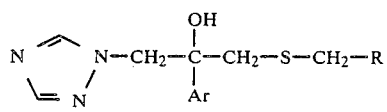 | >20 (p.o.) |

We claim:

1. A compound of the formula $$\text{imidazole-N-CH}_2\text{-C(OH)(Ar)-CH}_2\text{-S-CH}_2\text{-R}$$

or a pharmaceutically acceptable salt thereof wherein Ar is 2,4-dichlorophenyl; and R is phenyl, chlorophenyl, $C_{1-4}$ alkoxyphenyl, $C_{2-5}$ alkoxycarbonylphenyl, 2-furyl, 2-pyridyl, 1-methylimidazol-2-yl, 1-methyltetrazol-5-yl and 2-aminothiazol-4yl.

2. A compound as claimed in claim 1 wherein R is 2-furyl, 2-pyridyl, 1-methyl-tetrazol-5-yl, phenyl, 3- or 4-chlorophenyl, 4-methoxyphenyl, 4-carbomethoxyphenyl or 2-aminothiazol-4-yl.

3. The compound as claimed in claim 2 wherein R is 1-methyltetrazol-5-yl.

4. The compound as claimed in claim 2 wherein R is 2-pyridyl.

5. The compound as claimed in claim 2 wherein R is 4-chlorophenyl.

6. The compound as claimed in claim 2 wherein R is 2-aminothiazol-4-yl.

7. A pharmaceutical composition comprising an antifungally effective amount of a compound as claimed in claim 1, or a pharmaceutically acceptable salt thereof, together with a pharmaceutically acceptable diluent or carrier.

8. A method of treating a fungal infection in a human which comprises administering to said human an effective antifungal amount of a compound according to claim 1.

* * * * *